United States Patent [19]
Stock

[11] Patent Number: 5,612,896
[45] Date of Patent: Mar. 18, 1997

[54] METHOD FOR DETERMINING CHARACTERISTIC VARIABLES OF AN ELECTROCHEMICALLY CONVERTIBLE SUBSTANCE IN A GAS SAMPLE

[75] Inventor: Burkhard Stock, Lübeck, Germany

[73] Assignee: Drägerwerk Aktiengesellschaft, Lübeck, Germany

[21] Appl. No.: 361,514

[22] Filed: Dec. 22, 1994

[30] Foreign Application Priority Data

Dec. 23, 1993 [DE] Germany .......................... 43 44 196.3

[51] Int. Cl.$^6$ ............................................. G06G 7/19
[52] U.S. Cl. .......................... 364/497; 364/496; 364/499; 204/400; 205/775; 205/787
[58] Field of Search .................... 364/496–499; 73/23.3, 23.2, 23.23, 23.21, 23.36, 23.37; 422/83, 84, 89–92, 98, 119, 82.01, 82.02, 88; 436/900; 205/775, 787; 204/400

[56] References Cited

U.S. PATENT DOCUMENTS

| | | | |
|---|---|---|---|
| 3,555,260 | 1/1971 | Karohl | 73/23.23 |
| 4,770,026 | 9/1988 | Wolf | 73/23.3 |
| 5,048,321 | 9/1991 | Chow | 73/23.3 |
| 5,121,443 | 6/1992 | Tomlinson | 73/23.36 |
| 5,393,495 | 2/1995 | Forrester | 422/83 |

*Primary Examiner*—Ellis B. Ramirez
*Assistant Examiner*—Hal D. Wachsman
*Attorney, Agent, or Firm*—Walter Ottesen

[57] ABSTRACT

The invention is directed to a method for determining characteristic variables of an electrochemically convertible substance in a gas sample. The component of the substance in the gas sample is determined by integrating the total area I enclosed between a physical measurement variable i(t) and a reference line 1. The method is improved in that the concentration portion of the substance can be determined with a high long-term stability and an identification of the substance is possible. The method is carried out by determining the characteristic variables from an individual or several component integrals ($I_1$, $I_2$, $I_3$) as component areas of the total area I and/or of the sum of the component integrals and/or of the ratio of the component integrals $I_1/I_2$ and/or of the ratio of the maximum value $i_{max}$ and the component integral $I_2$.

18 Claims, 8 Drawing Sheets

FIG. 7

| | Ethanol | Methanol | Isopropanol |
|---|---|---|---|
| P | 1 | 0.35 | 1.27 |
| $I_1/I$ | 0.57 | 0.45 | 0.56 |
| $I_2/I$ | 0.26 | 0.38 | 0.26 |
| $t_a$ | 32 | 156 | 25 |
| $\dfrac{P}{I_2/I}$ | 3.84 | 0.92 | 4.88 |
| $\dfrac{I_1}{I_2}$ | 2.19 | 1.18 | 2.15 |

$$P = \frac{i\max(\text{Ethanol, Methanol, Isopropanol})}{i\max(\text{Ethanol})}$$

METHOD FOR DETERMINING CHARACTERISTIC VARIABLES OF AN ELECTROCHEMICALLY CONVERTIBLE SUBSTANCE IN A GAS SAMPLE

FIELD OF THE INVENTION

The invention relates to a method for determining characteristic variables of an electrochemically convertible substance in a gas sample. The substance generates a physical measurement variable in a measuring cell. This variable changes as a function of time and increases from a reference line to a maximum value and returns to the reference line. The component of the substance in the gas sample is computed from the measurement variable in an evaluation circuit from the integration over the total area enclosed between the reference line and the function value of the physical measurement variable.

BACKGROUND OF THE INVENTION

An arrangement for measuring the concentration of alcohol as a substance to be detected in breathing gas is disclosed in U. S. Pat. No. 4,770,026. In the known arrangement, a fuel cell is subjected to a gas sample having an alcohol vapor component and the physical measurement variable i(t), which is obtained by the electrochemical conversion, is supplied to an evaluation circuit which determines a measurement value proportional to the alcohol vapor concentration. The measurement value is determined by integrating the signal trace of the physical measurement value as a function of time (t). When the measuring cell is charged with alcohol vapor, the measurement signal first increases starting from a reference line, passes through a maximum value $i_{max}$ and returns again to a minimum value in the vicinity of the reference line after the complete electrochemical conversion. The area enclosed between the function value of the measurement signal and the reference line is proportional to the concentration of the alcohol vapor in the gas sample.

In the known measuring cell, the trace of the curve of the measurement signal changes with increasing deterioration of the measuring cell. Accordingly, the curve profile becomes flatter and wider in the course of the use time of the measuring cell. A similar change of the curve trace of the measurement signal occurs also after several measuring cycles occurring in rapid succession. This signal change is at least partially reversible after a longer recovery phase. For determining the concentration component of the alcohol vapor in the gas sample, integration takes place over the entire measurement signal trace. For this reason, the changes of the curve profile operate on the area content and therefore also on the measurement accuracy so that calibrating cycles must be repeatedly carried out with a gas sample of a known alcohol concentration. Calibration cycles of this kind make using the apparatus difficult especially when the measuring cell is subjected to gas at short time intervals. Furthermore, the composition of the substance to be detected must be known for the known evaluation method.

SUMMARY OF THE INVENTION

It is an object of the invention to improve the evaluating method for the measurement variable of an electrochemical measuring cell in such a manner that the concentration component of the substance to be detected can be determined with a high long-term stability over the service life of the measuring cell and that, additionally, an identification of the substance is possible.

The method of the invention is for determining characteristic variables of an electrochemically convertible substance in a gas sample and includes the steps of: generating a physical measurement variable i(t) which changes as a function of time to define a curve and which increases from a reference line up to a maximum value ($i_{max}$, P) and returns to the reference line; computing the portion of the substance in the gas sample in an evaluation circuit by integrating over an area (I) enclosed between the reference line and the curve; subdividing the area into component areas representing respective component integrals ($I_1$, $I_2$, $I_3$, $I_4$); and, determining a first one of the characteristic variables as indicative of the substance or a second one of the characteristic variables as indicative of the identity of the substance from at least one of the component integrals ($I_1$, $I_2$, $I_3$, $I_4$).

The advantage of the invention essentially is that the entire area I between the function value of the physical measurement variable, which in the present case is the sensor current i(t), and a reference line for the evaluation method is no longer used exclusively; instead, component areas as component integrals of the total integral are used from which different characteristic variables of the substance to be detected can be determined. The substance can, for example, be the concentration component in the gas sample or the nature of the material of the substance. In known sensors, the total area enclosed between the measurement value and the reference line changes in the course of use of the measuring cell so that calibration cycles must be carried out more often. It was surprisingly found that specific component areas or ratios of component areas remain practically unchanged in the course of the service life. Based on this fact, a more precise analysis of the substance to be investigated in the gas sample, independently of the state of deterioration of the measuring cell, can be made by evaluating the area content of the component areas.

The integrating limits referred to the component integrals are set to predetermined percentage portions of the physical measurement variable referred to the maximum value. The maximum value of the pulse-like running measurement variable is relatively easily determined. For this reason, the integration limits can be clearly given as a percentage amplitude drop from the maximum value.

In an advantageous manner, the component integral $I_1$ provides the area content of the component area from the start of the electrochemical conversion beyond the maximum value $i_{max}$ to the drop of the measurement value i(t) to 75% of the maximum value. The component integral $I_2$ which continues therefrom extends from the percentage component of the maximum value of the measurement value of 75% to 25% and the component integral $I_3$ includes portions of $I_1$ and $I_2$ between the percentage components 95% and 25%. The component integral $I_4$ lies between the amplitude drop of the measurement variable from 25% to 6%.

In an advantageous manner, the concentration component of the substance in the gas sample is computed as a first characteristic variable of the substance from the component integral $I_3$. Experiments have shown that the component integral $I_3$ exhibits a very slight dependency with respect to deterioration and with respect to the measuring cell being repeatedly subjected to gas samples.

Also in an advantageous manner, the substance can be identified, as a second characteristic variable of the substance, by forming the ratio of the component integrals $I_1/I_2$ or the ratio of the relative maximum value P and the component integral $I_2$ referred to the total integral I. In this way, mixed states of different substances can also be detected. The dimensionless relative maximum value P is identified in the following with maximum value P and indicates the maximum sensor current $i_{max}$ referred to that of ethanol; that is, P has the value "1" for ethanol.

The identification of the substance can be advantageously supported by including a so-called decay time $t_a$. This decay time $t_a$ is the time between the amplitude drop of the measurement variable i(t) from 50% to 6% of the maximum value $i_{max}$. The decay time $t_a$ is a measure for the speed of conversion of the substance within the electrochemical measuring cell.

In an advantageous embodiment of the method of the invention, an evaluation circuit processes the physical measurement value supplied by the measuring cell. According to this embodiment, at least one integrator and an amplitude detector are provided and the amplitude detector sets the integration limits for the integrator. The amplitude detector determines integration limits $t_1$ to $t_5$ from the increase of the sensor current from the reference line and from the drop of the sensor current to a predetermined percentage portion of the maximum value $i_{max}$. The component integrals $i_1$ to $i_4$ and also the total integral I between $t_1$ to $t_5$ are computed with the integration limits $t_1$ to $t_5$. The integrator and the amplitude detector can also be components of a microprocessor.

BRIEF DESCRIPTION OF THE DRAWINGS

The invention will now be described with reference to the drawings wherein:

FIG. 7 is a tabular listing of variables for identifying substances to be detected; and, FIG. 8 is a block circuit diagram of an arrangement for carrying out the method of the invention.

DESCRIPTION OF THE PREFERRED EMBODIMENTS OF THE INVENTION

Figure 1:
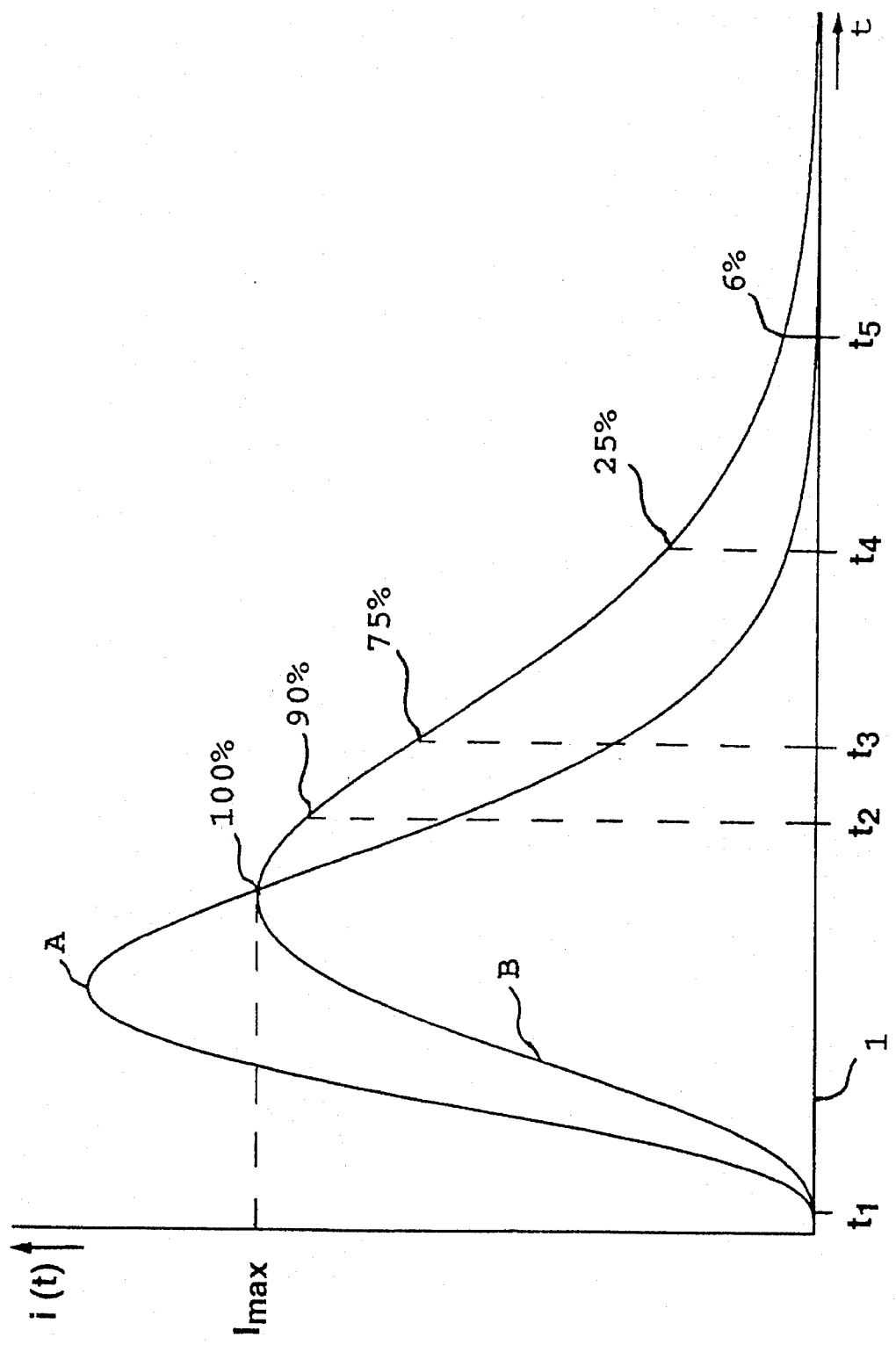
FIG. 1 is a time-dependent trace of the sensor current i(t) of an electrochemical measuring cell.

FIG. 1 shows the time-dependent trace of the sensor current i(t) of an electrochemical measuring cell (not shown in FIG. 1) when subjected to a gas sample containing an electrochemically convertible substance. The electrochemically convertible substance is, in this case, alcohol and the gas sample is breathing gas. Curve A of FIG. 1 is the trace of the sensor current i(t) as a physical measurement variable of a factory-new measuring cell; whereas, curve B indicates the sensor current i(t) of a measuring cell which has already been subjected to gas several times. The following observations are made exemplary with respect to curve B. The time (t) is plotted on the abscissa of the coordinate system shown in FIG. 1 and the sensor current i(t) is plotted on the ordinate.

At time point $t_1$, the measuring cell is subjected to alcohol vapor whereupon the sensor current i(t) first increases to its maximum value $i_{max}$ and, after the electrochemical conversion of all alcohol molecules, drops again to the original value. After exceeding the maximum sensor current $i_{max}$, the sensor current drops as follows: at time point $t=t_2$, to 90% of maximum value; at $t=t_3$, to 75%; at $t=t_4$, to 25%; and at $t=t_5$, to 6% of the maximum sensor current.

In known arrangements, the sensor current i(t) is integrated over the entire time interval between $t_1$ and $t_2$ with respect to a reference line 1, which in the present case, is coincident with the abscissa of the coordinate system. With this integration, in the known arrangements, a measurement value is computed which is proportional to the concentration of alcohol to be determined. The integration between $t_1$ and $t_5$ results in a total integral I. The sensor currents i(t) at the start and at the end of the electrochemical conversion at the time points $t_1$ and $t_5$ have a finite magnitude (for example, 6% at $t_5$) in order to limit in time the integration for practical reasons. A comparison of the curves A and B shows that the respective areas beneath the curves A and B change during the measurement use. For curve B, the maximum value $i_{max}$ is less compared to curve A of the factory-new measuring sensor and the overall curve B is flatter.

Figure 2:
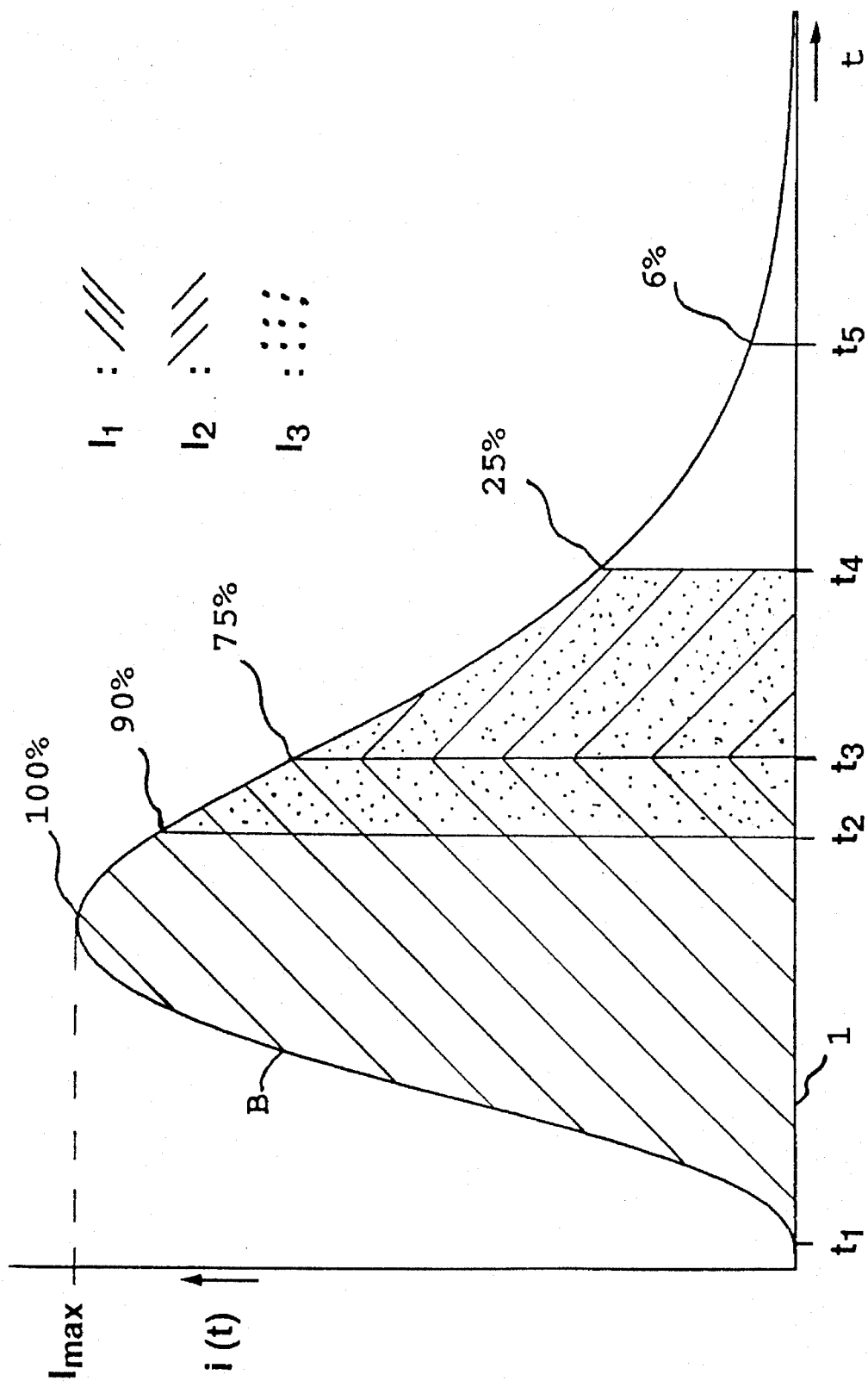
FIG. 2 is a schematic showing the formation of component integrals $I_1$, $I_2$, $I_3$ as a function of the sensor current i(t)

In FIG. 2, three component integrals $I_1$, $I_2$ and $I_3$ are shown as component areas of the total integral I for curve B between the function value of the sensor current i(t) and the reference line (1). The component integral $I_1$ is formed between the integration limits $t_1$ and $t_3$ and component integral $I_2$ is formed between limits $t_3$ and $t_4$ and the component integral $I_3$ between the limits $t_2$ and $t_4$. The same elements are identified here with the same symbols as were used in FIG. 1.

Figure 3:
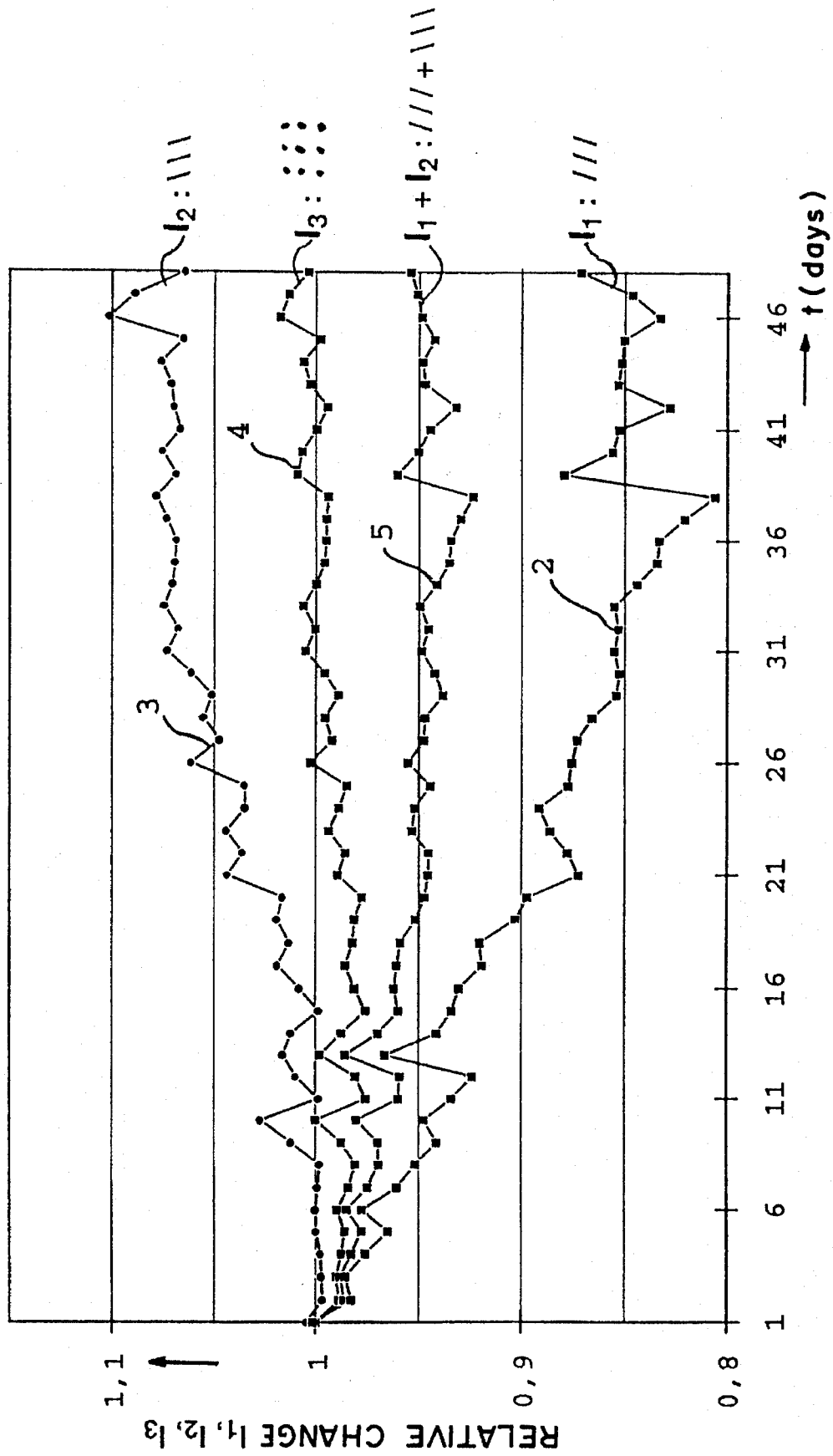
FIG. 3 is a schematic showing the relative change of the component integrals of FIG. 2 in dependence upon the use time of the measuring cell.

In FIG. 3, the values of the component integrals $I_1$, $I_2$ and $I_3$ of FIG. 2 are shown in dependence upon the use time of the measuring cell. The use time (t) in days is plotted along the abscissa of the coordinate system and the relative change of the component integrals relative to the initial state at the start of measurements is plotted along the ordinate. The curves (2, 3, 4, 5) show the component integrals $I_1$, $I_2$, $I_3$ and $I_1+I_2$ as a function of time. While the component integral $I_1$ (curve 2) drops greatly with increasing time (t), the component integral $I_2$ (curve 3) increases. The sum of the component integrals $I_1$ and $I_2$ (curve 5) still shows a certain drop in dependence upon time (t). However, if one observes the component integral $I_3$ (curve 4) between the drop of the sensor current i(t) from 90% to 25%, then this value remains almost constant. The method of the invention for determining the concentration component of the substance to be detected in the gas sample then comprises utilizing the component integral $I_3$ as a first characteristic variable of the substance and to carry out the integration only in that region in which the sensor current i(t) drops from approximately 90% to approximately 25% of the maximum value $i_{max}$.

Figure 4:
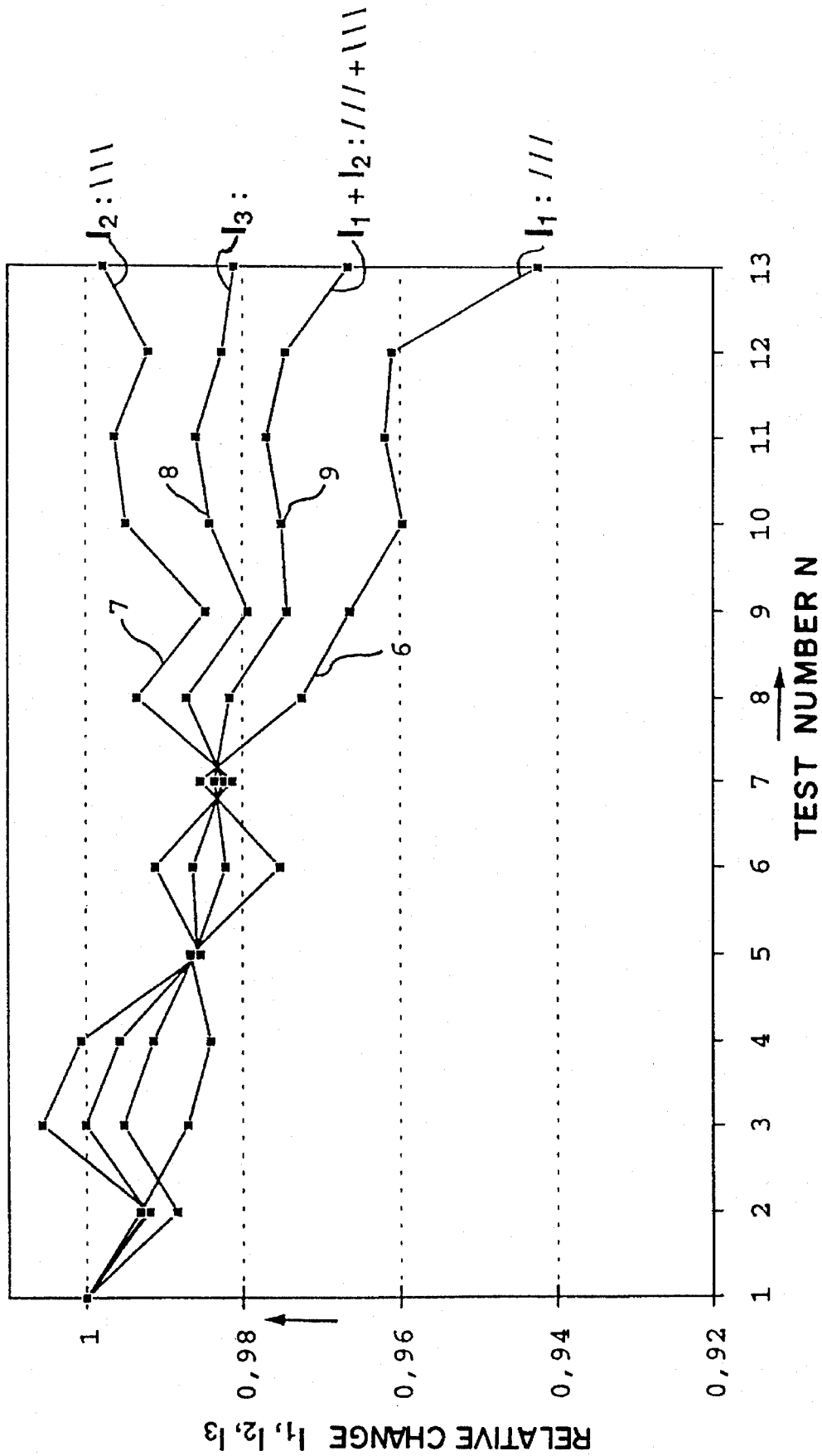
FIG. 4 is a schematic showing the relative change of the component integrals of FIG. 2 in dependence upon the number of measuring cycles, that is, the test number N.

The component integral $I_3$ does not vary in the course of use of the measuring cell. This can be confirmed with further experiments. Accordingly, in FIG. 4, the component integrals $I_1$, $I_2$, $I_3$ and $I_1+I_2$ are shown as curves (6, 7, 8, 9), respectively, in dependence upon the number of measuring cycles when multiply subjected to gas, the test number N. The relative change referred to the starting state is again plotted along the ordinate. Here too, the component integral $I_1$ (curve 6) drops continuously, the component integral $I_2$ (curve 7) first drops and then shows an increasing tendency; whereas, the sum of the component integrals $I_1$ and $I_2$ (curve 9) drops continuously as does curve 6. In contrast, the value of the component integral $I_3$ (curve 8) becomes stable at approximately 0.98 of the starting state. A comparison of FIGS. 3 and 4 confirms the surprisingly found fact that the component integral $I_3$ (curves 4 and 8) shows the least fluctuating band in the course of service time of the measuring cell and of the number N of the measuring cycles and is therefore especially suitable for determining the concentration portion of alcohol vapor in the gas sample.

Figure 5:
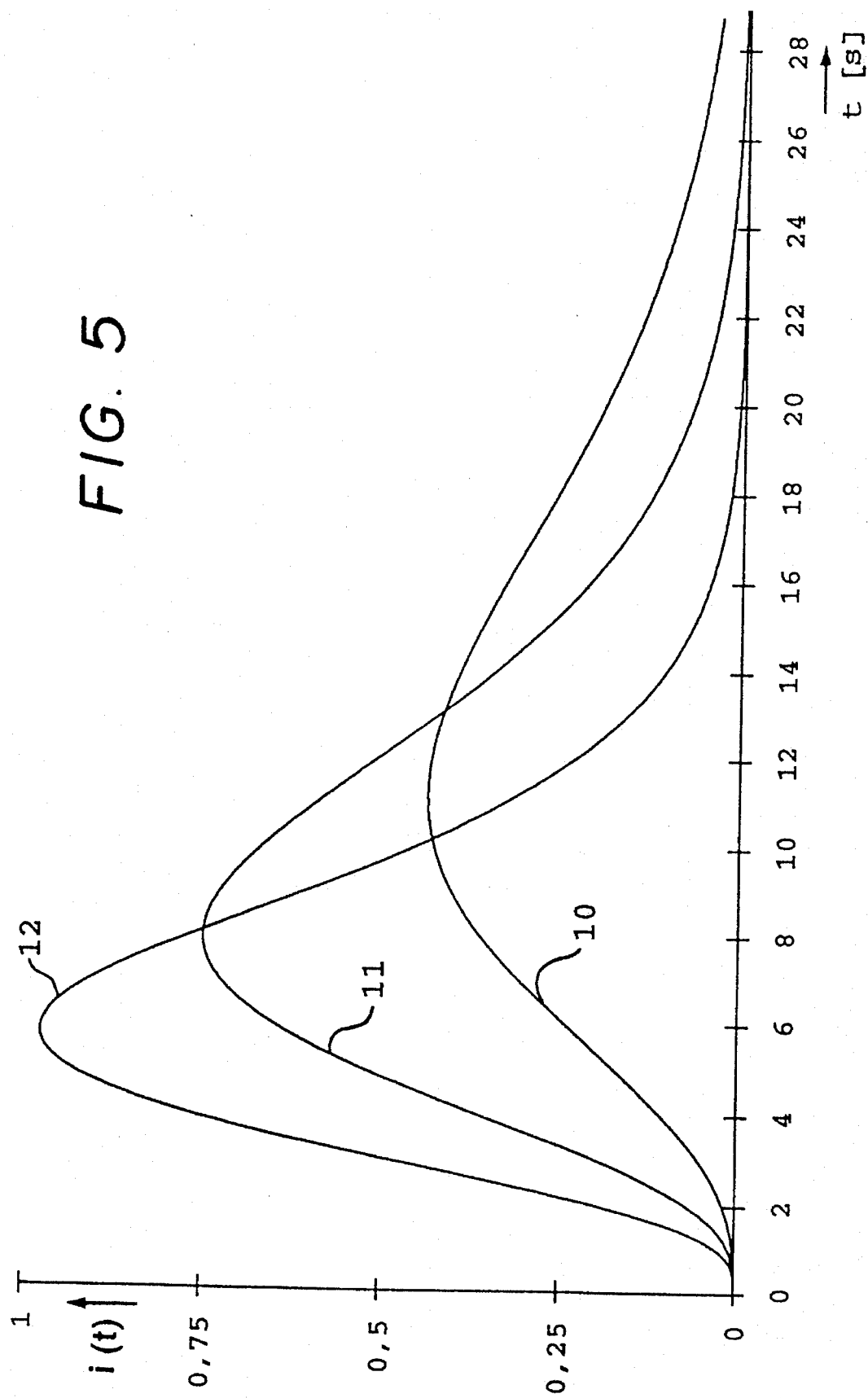
FIG. 5 shows the time-dependent trace of the sensor current i(t) of an electrochemical measuring cell which is subjected to gas containing different alcohols.

In FIG. 5, three current curves (10, 11, 12) of the sensor current i(t) are shown for the substances methanol, ethanol and isopropanol. For methanol (curve 10), the speed of conversion in the measuring cell is only one fifth as fast as for ethanol (curve 11). The speed of conversion for isopropanol (curve 12) is approximately 30% faster than for ethanol (curve 11).

Figure 6:
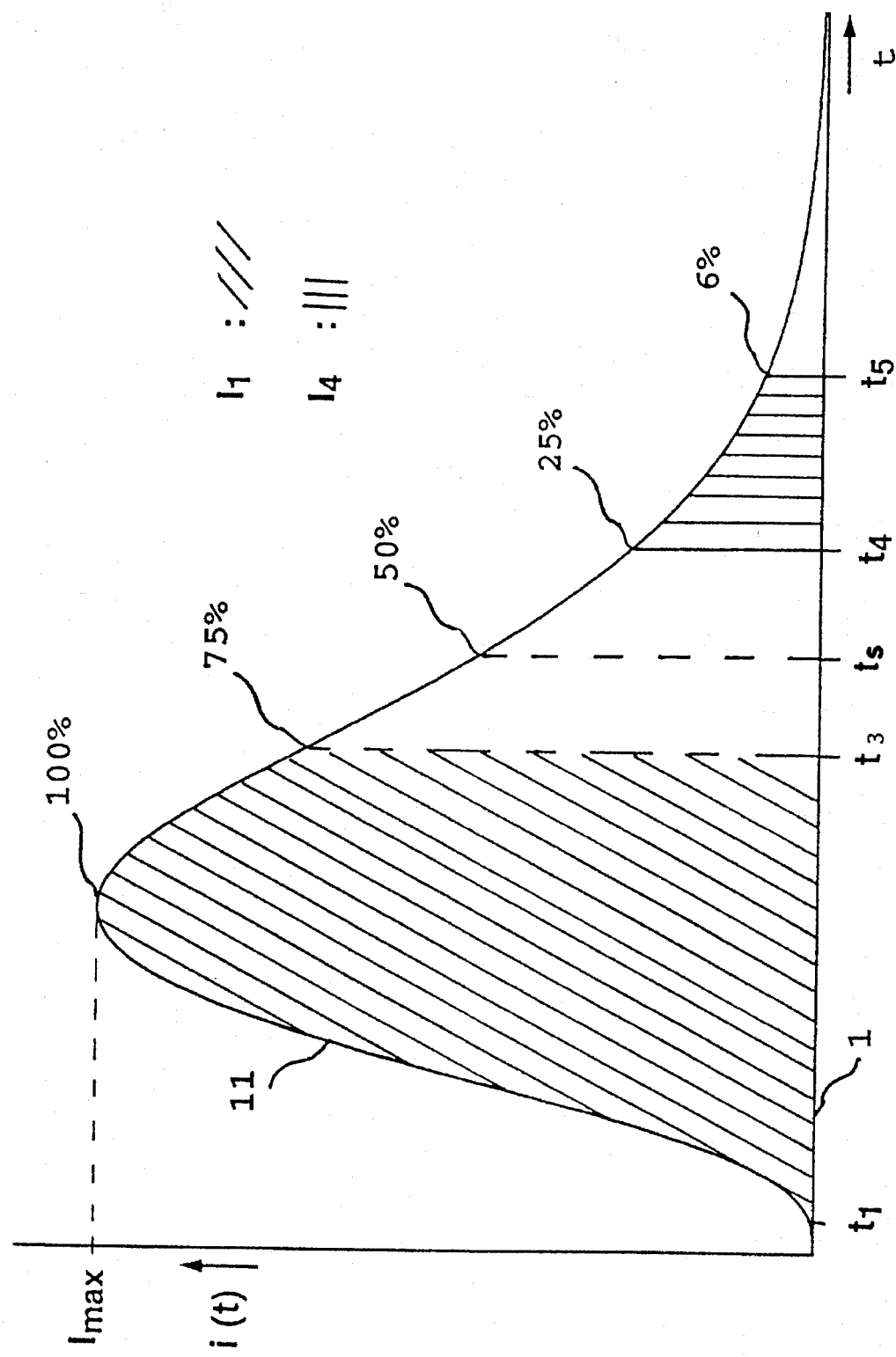
FIG. 6 is a schematic showing the formation of component integrals $I_1$ and $I_4$ with the sensor current according to FIG. 5.

In FIG. 6, the component integrals $I_1$ and $I_4$ are shown below one of the current curves (10, 11, 12). For a better overview, only the current curve 11 is shown. The component integral $I_1$ includes the area content between the current curve 11 and the reference line 1 within the integration limits of $t=t_1$ to $t=t_3$. The time point $t_3$ defines the time point of the drop of the current curve 11 to 75% of the maximum value $i_{max}$ and the component integral $I_4$ is formed between the integration limits $t=t_4$ and $t=t_5$ during the drop of the current curve 11 from 25% to 6% of the maximum value $i_{max}$. Furthermore, a so-called decay time $t_a$ is introduced which indicates the time interval for the drop of the sensor current i(t) from 50% ($t=t_{31}$) to 6% ($t=t_5$) of the maximum value $i_{max}$, that is, $t_a=t_5-t_5$.

The total integral I of the current curve (10, 11 or 12) is computed within the integration limits of $t=t_1$ to $t=t_5$.

In FIG. 7, the component integrals $I_1$ and $I_2$ are shown in tabular form referred to the total integral I. The table also shows the maximum values P, the decay times $t_a$ and the ratios of the maximum values P to the component integral $I_2$, namely $P/(I_2/I)$ and the ratios of the component integrals $I_1/I_2$ for the current curves (10, 11, 12), that is, for the substances methanol, ethanol and isopropanol. For a better overview, several dimensionless reference variables are shown in FIG. 7. Thus, a dimensionless maximum value P is used which is referred to the maximum value $i_{max}$ of ethanol and the component integrals $I_1$ and $I_2$ are likewise shown dimensionless and are referred to the particular total integral I.

From FIG. 7, it can be seen that the variables $P/(I_2/I)$ and $I_1/I_2$ as well as $t_a$ as the second characteristic variable of the substance are very much specific to substance and can be used for identifying the substance to be detected. Thus, the second characteristic variable $I_1/I_2$ has an especially good long-term uniformity and changes only slightly with increasing time of use of the electrochemical measuring cell. In practical use, and after a new measuring cell is connected, one proceeds by carrying out respective calibrating cycles with the substances ethanol, methanol and isopropanol in order to determine the characteristic variables listed in FIG. 7 and to store the same in a memory unit not shown in FIG. 7.

If, during the measuring operation, an unknown substance is analyzed, then, for example, the second characteristic variables ($P/(I_2/I)$ and $I_1/I_2$) of the unknown substance are first determined and compared to the stored values. The substance to be detected is identified when the corresponding stored and measured characteristic variables are coincident. Thereafter, the concentration component of the substance in the gas sample is computed with the component integral $I_3$ (FIG. 2).

Figure 8:
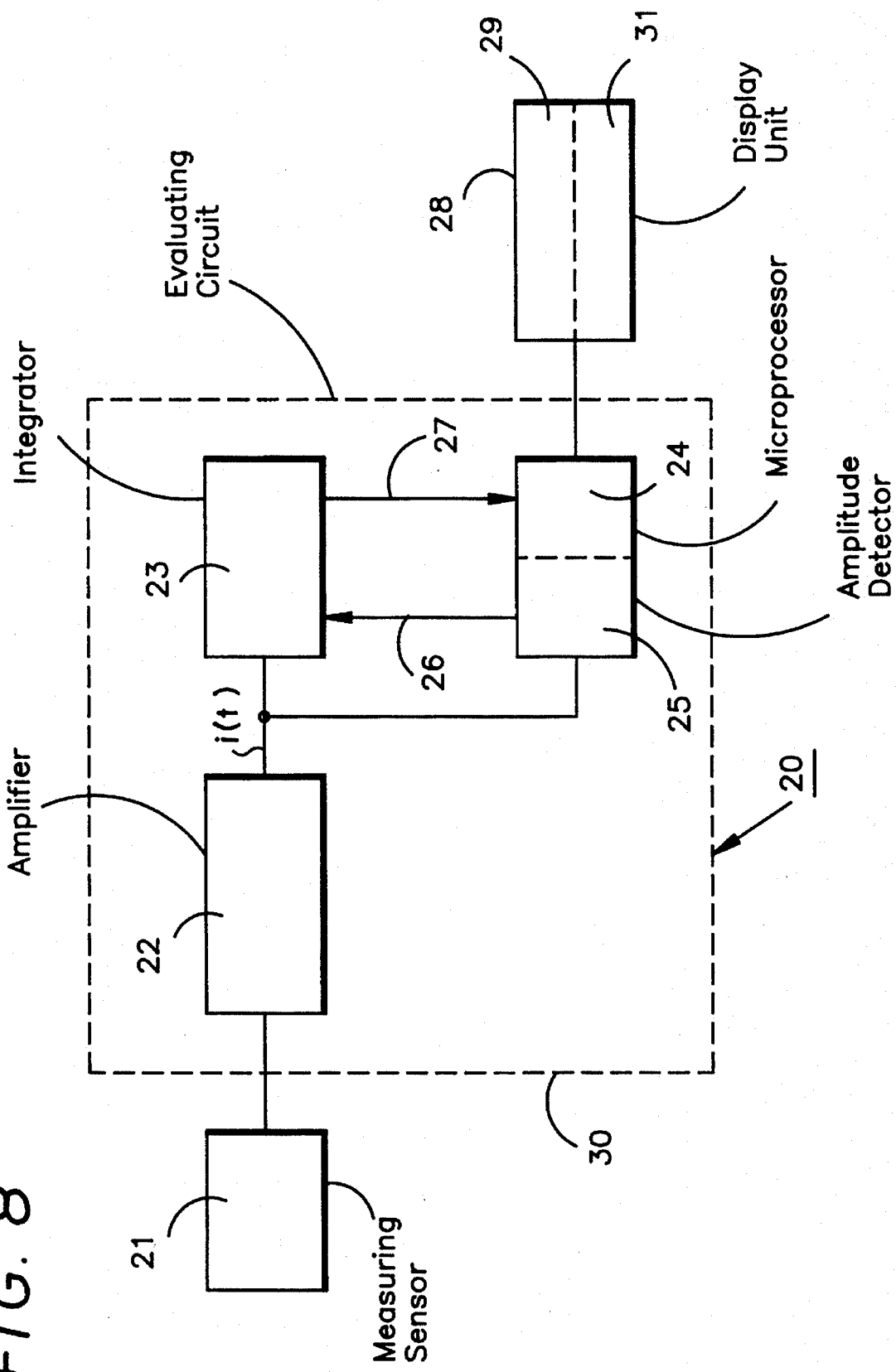

In FIG. 8, an arrangement 20 according to the invention is shown for determining the characteristic variables of the electrochemically convertible substances. An electrochemical measuring sensor 21 is connected via an amplifier 22 to an integrator 23 and a microprocessor 24. When the measuring sensor 21 is subjected to gas containing the substance to be detected, then a sensor current i(t) corresponding to the substance appears at the output of the amplifier 22. Component integrals $I_1$, $I_2$, $I_3$ and $I_4$ are formed from this sensor current i(t) with the aid of integrator 23 and the microprocessor 24. The integration limits $t_1$ to $t_5$ corresponding to the integrals are generated in an amplitude detector 25 within the microprocessor 24 and outputted via a first signal line 26 to the integrator 23.

The amplitude detector 25 determines the integration limits $t_1$ to $t_5$ from the increase of the sensor current i(t) from the reference line 1 (FIG. 2) and the drop of the sensor current i(t) to the predetermined percentage portions of the maximum value $i_{max}$ of 90%, 75%, 25% and 6%. The component integrals $I_1$ to $I_4$ and the total integral I are computed with the integration limits $t_1$ to $t_5$. The component integrals $I_1$ to $I_4$ computed in integrator 23 and the total integral I are read into the microprocessor 24 via a second signal line 27.

All memory and computing operations are carried out within the microprocessor 24. The amplifier 22, the integrator 23 and the microprocessor 24 together with the amplitude detector 25 conjointly define an evaluating circuit 30 for the measuring sensor 21. Characteristic variables of the substance to be detected are indicated on a display unit 28 connected downstream of the evaluating circuit 30. More specifically, the concentration portion of the substance in the gas sample is displayed as a first characteristic variable 29 and the identity of the substance is displayed as a second characteristic variable 31.

It is understood that the foregoing description is that of the preferred embodiments of the invention and that various changes and modifications may be made thereto without departing from the spirit and scope of the invention as defined in the appended claims.

What is claimed is:

1. A method for determining characteristic variables of an electrochemically convertible substance in a gas sample, the method comprising the steps of:

utilizing an electrochemical measuring sensor generating a sensor current i(t) which changes as a function of time to define a curve and which increases from a reference current line up to a maximum value ($i_{max}$) and returns to said reference current line;

computing the portion of said substance in said gas sample in an evaluation circuit by integrating over an area (I) enclosed between said reference current line and said curve;

subdividing said area into component areas representing respective first to fourth component integrals ($I_1$, $I_2$, $I_3$, $I_4$); and, determining at least one of a first of said characteristic variables as indicative of the concentration of said substance and a second of said characteristic variables as indicative of the identity of said substance from at least one of said component integrals ($I_1$, $I_2$, $I_3$, $I_4$) wherein the total area of said component integrals ($I_1$, $I_2$, $I_3$, $I_4$) is less than said area (I).

2. The method of claim 1, wherein first to fifth integration limit time points ($t_1$, $t_2$, $t_3$, $t_4$, $t_5$) delimit said component integrals ($I_1$, $I_2$, $I_3$, $I_4$) to predetermined percentage components of said sensor current $i(t)$ from said maximum value ($i_{max}$).

3. The method of claim 2, wherein:

the electrochemical conversion of said substance begins at time point ($t=t_1$) and said sensor current $i(t)$ drops to approximately 75% of said maximum value ($i_{max}$) at time point ($t=t_3$); and, said first component integral $I_1$ is delimited by said first time point ($t=t_1$) and said third time point ($t=t_3$); and, wherein:

said sensor current $i(t)$ drops to 25% of said maximum value ($i_{max}$) at the fourth time point ($t=t_4$); and, said second component integral $I_2$ is delimited by said third time point ($t=t_3$) and said fourth time point ($t=t_4$); and, wherein:

said sensor current $i(t)$ drops to approximately 90% of said maximum value ($i_{max}$) at said second time point ($t=t_2$); and, said third component integral $I_3$ is delimited by said second time point ($t=t_2$) and said fourth time point ($t=t_4$); and, wherein:

said sensor current $i(t)$ drops to approximately 6% of said maximum value ($i_{max}$) at said fifth time point ($t=t_5$); and, said fourth component integral $I_4$ is delimited by said fourth time point ($t=t_4$) and said fifth time point ($t=t_5$).

4. The method of claim 3, wherein the concentration of said substance in said gas sample is computed as said first characteristic variable from said third component integral $I_3$.

5. The method of claim 3, wherein the identity of said substance in said gas sample is formed as said second characteristic variable from said ratio ($I_1/I_2$) of said first and second component integrals.

6. The method of claim 5, wherein said sensor current $i(t)$ drops to 50% of said maximum value ($i_{max}$) at an additional time point ($t=t_s$); and, said second characteristic variable is formed by considering a decay time $t_a$ between said additional time point ($t=t_s$) and said fifth time point ($t=t_5$).

7. The method of claim 3, wherein the identity of said substance in said gas sample is formed as said second characteristic variable from a ratio of said maximum value $i_{max}$ and said second component integral $I_2$.

8. The method of claim 7, wherein said sensor current $i(t)$ drops to 50% of said maximum value ($i_{max}$) at an additional time point ($t=t_s$); and, said second characteristic variable is formed by considering a decay time $t_a$ between said additional time point ($t=t_s$) and said fifth time point ($t=t_5$).

9. The method of claim 3, wherein the identity of said substance in said gas sample is formed as said second characteristic variable from said ratio of said first and second component integrals and from a ratio of said maximum value $i_{max}$ and said second component integral $I_2$.

10. The method of claim 9, wherein said physical measurement variable $i(t)$ drops to 50% of said maximum value ($i_{max}$) at an additional time point ($t=t_s$); and, said second characteristic variable is formed by considering a decay time $t_a$ between said additional time point ($t=t_s$) and said fifth time point ($t=t_5$).

11. A method for determining characteristic variables of an electrochemically convertible substance in a gas sample, the method comprising the steps of:

utilizing an electrochemical measuring sensor generating a sensor current $i(t)$ which changes as a function of time to define a curve and which increases from a reference current line up to a maximum value ($i_{max}$) and returns to said reference current line;

computing the portion of said substance in said gas sample in an evaluation circuit by integrating over an area (I) enclosed between said reference current line and said curve;

subdividing said area into component areas representing respective first to fourth component integrals ($I_1$, $I_2$, $I_3$, $I_4$);

determining at least one of a first of said characteristic variables as indicative of the concentration of said substance and a second of said characteristic variables as indicative of the identity of said substance from at least two of said component integrals ($I_1$, $I_2$, $I_3$, $I_4$); and, forming the sum of said first and second component integrals ($I_1+I_2$) and determining said first and second characteristic variables also from said sum of said first and second component integrals ($I_1+I_2$).

12. The method of claim 11, forming a ratio ($I_1/I_2$) of said first and second component integrals and determining said first and second characteristic variables also from said ratio ($I_1/I_2$).

13. The method of claim 12, said ratio being a first ratio; forming a second ratio of said maximum value ($i_{max}$) and one of said component integrals ($I_1$, $I_2$, $I_3$ or $I_4$) and determining said first and second characteristic variables also from said second ratio.

14. A method for determining a characteristic variable of an electrochemically convertible substance in a gas sample with the electrochemical conversion beginning at a time point ($t=t_1$), the method comprising the steps of:

utilizing an electrochemical measuring sensor to generate a sensor current $i(t)$ which changes as a function of time to define a curve and which increases from a reference current line up to a maximum value ($i_{max}$) and returns to said reference current line and said sensor current $i(t)$ dropping to approximately 90% of said maximum value ($i_{max}$) at a second time point ($t=t_2$) and to approximately 25% of said maximum value ($i_{max}$) at a further time point ($t=t_4$);

integrating over an area (I) enclosed between said reference current line and said curve in an evaluation circuit;

subdividing said area (I) to obtain a component area defining a particular component integral ($I_3$);

delimiting said particular component integral $I_3$ in said evaluation circuit between said second time point ($t=t_2$) and said further time point ($t=t_4$); and, computing said characteristic variable as indicative of the concentration of said substance from said component integral ($I_3$).

15. An arrangement for determining characteristic variables of an electrochemically convertible substance in a gas sample, the arrangement comprising:

means for generating a sensor current $i(t)$ which changes as a function of time to define a curve and which increases in amplitude from a reference current line up to a maximum value ($i_{max}$) and then decreases in amplitude to said reference current line;

amplitude detector means for determining a plurality of integration limit time points ($t_1$, $t_2$, $t_3$, $t_4$) from the increase or decrease in said amplitude; and, integrator means for integrating over an area (I) enclosed between said curve and said reference current line for forming at least individual component integrals ($I_1$, $I_2$, $I_3$, $I_4$) as component areas of said area (I) utilizing said integration limit time points ($t_1$, $t_2$, $t_3$, $t_4$) wherein the total area of the component areas is less than said area (I).

16. A method for determining a characteristic variable of an electrochemically convertible substance in a gas sample with the electrochemical conversion beginning at a time point ($t=t_1$), the method comprising the steps of:

utilizing an electrochemical measuring sensor to generate a sensor current $i(t)$ which changes as a function of time to define a curve and which increases from a reference current line up to a maximum value ($i_{max}$) and returns to said reference current line and said sensor current $i(t)$ dropping to approximately 75% of said maximum value ($i_{max}$) at a later time point ($t=t_3$) and to approximately 6% of said maximum value ($i_{max}$) at a further time point ($t=t_5$);

integrating over an area (I) enclosed between said reference current line and said curve in an evaluation circuit;

subdividing said area (I) to obtain an area defined by the composite of two component integrals ($I_2+I_4$);

delimiting said two component integrals $I_{(2}+I_4)$ in said evaluation circuit between said later time point ($t=t_3$) and said further time point ($t=t_5$); and, computing said characteristic variable as indicative of the concentration of said substance from at least a portion of said composite of said two component integrals ($i_2+I_4$).

17. The method of claim 16, wherein said characteristic variable is computed as indicative of the concentration of said substance from all of said composite of said two component integrals ($I_2+I_4$).

18. A method for determining characteristic variables of an electrochemically convertible substance in a gas sample, the method comprising the steps of:

utilizing an electrochemical measuring sensor generating a sensor current $i(t)$ which changes as a function of time to define a curve and which increases from a reference current line up to a maximum value ($i_{max}$) and returns to said reference current line;

computing the portion of said substance in said gas sample in an evaluation circuit by integrating over an area (I) enclosed between said reference current line and said curve;

subdividing said area into component areas representing respective first to fourth component integrals ($I_1$, $I_2$, $I_3$, $I_4$);

determining at least two of a first of said characteristic variables as indicative of the concentration of said substance and a second of said characteristic variables as indicative of the identity of said substance from at least one of said component integrals ($I_1$, $I_2$, $I_3$, $I_4$) wherein the total area of said component integrals ($I_1$, $I_2$, $I_3$, $I_4$) is less than said area (I); and, forming a ratio ($I_1/I_2$) of said first and second component integrals and determining said second characteristic variable from said ratio ($I_1/I_2$).

* * * * *

UNITED STATES PATENT AND TRADEMARK OFFICE
CERTIFICATE OF CORRECTION

PATENT NO.  : 5,612,896
DATED       : March 18, 1997
INVENTOR(S) : Burkhard Stock It is certified that error appears in the above-indentified patent and that said Letters Patent is hereby corrected as shown below:

In column 5, line 33, please delete "$t_a = t_5 - t_5$" and insert -- $t_a = t_5 - t_s$ -- therefor.

In column 9, line 19, please delete "$I (_2 + I_4)$" and insert -- $(I_2 + I_4)$ -- therefor.

In column 9, line 25, please delete "$(i_2 + I_4).$" and insert -- $(I_2 + I_4)$ -- therefor.

Signed and Sealed this

Tenth Day of June, 1997

Attest:

BRUCE LEHMAN

*Attesting Officer*     *Commissioner of Patents and Trademarks*